United States Patent [19]
Warner et al.

[11] Patent Number: 5,770,084
[45] Date of Patent: Jun. 23, 1998

[54] POLYMERIZED CHIRAL MICELLES FOR CHIRAL SEPARATIONS

[75] Inventors: Isiah M. Warner, Baton Rouge, La.; Jian Wang, Somerset, N.J.

[73] Assignee: Board of Supervisors of Louisiana State University and Agricultural and Mechanical College, Baton Rouge, La.

[21] Appl. No.: 698,351

[22] Filed: Aug. 15, 1996

Related U.S. Application Data

[60] Provisional application No. 60/029,184 Aug. 16, 1995.
[51] Int. Cl.$^6$ ................................................ B01D 15/08
[52] U.S. Cl. ..................... 210/635; 210/634; 210/649; 210/656; 210/198.2; 95/88; 204/451
[58] Field of Search ......................... 95/82, 88; 204/602, 204/601, 603, 604, 605, 451, 452, 453, 454, 455, 456; 210/635, 634, 649, 656, 198.2

[56] References Cited

U.S. PATENT DOCUMENTS

| | | | |
|---|---|---|---|
| 4,516,984 | 5/1985 | Warner | 55/16 |
| 4,688,901 | 8/1987 | Albert | 350/350 S |

FOREIGN PATENT DOCUMENTS

| | | | |
|---|---|---|---|
| 04149205 | 5/1992 | Japan | 210/198.2 |
| 04149206 | 5/1992 | Japan | 210/198.2 |

OTHER PUBLICATIONS

D. Armstrong, "Optical Isomer Separation by Liquid Chromatography," Anal. Chem. vol. 59, pp. 84A–91A (1987).
R. J. Baczuk et al., "Liquid Chromatographic Resolution of Racemic β-3,4-Dihydroxyphenylalanine," J. Chromatogr., vol. 60, pp. 351–361 (1971).
E. Gassmann et al., "Electrokinetic Separation of Chiral Compounds," Science, vol. 230, pp. 813–814 (1985).
R. Kuhn et al., "Chiral Separation by Capillary Electrophoresis," Chromatographia, vol. 34, pp. 505–512 (1992).

(List continued on next page.)

*Primary Examiner*—Ernest G. Therkorn
*Attorney, Agent, or Firm*—John H. Runnels

[57] ABSTRACT

Chiral separations can be enhanced through the use of polymerized chiral micelles. Because polymerized micelles eliminate much of the complex dynamic behavior associated with conventional micelles, polymerized chiral micelles have stronger chiral recognition properties than do otherwise-identical, "conventional" or non-polymerized chiral micelles. Recovery of chiral ligands from polymerized chiral micelles is often easier, as the chiral ligands may typically be recovered by simple extraction with an appropriate organic solvent. By contrast, recovering the solute from a conventional, non-polymerized micellar medium by extraction with an organic solvent frequently results in the formation of troublesome emulsion systems. Polymerized chiral micelle systems are therefore beneficial in both preparative-scale and process-scale separations. Polymerized chiral micelles have no critical micelle concentration, allowing lower concentrations to be used in micellar electrokinetic capillary chromatography, which in turn reduces the otherwise deleterious heat that can be generated.

14 Claims, 8 Drawing Sheets

OTHER PUBLICATIONS

S. Terabe et al., "Chiral Separation by Electrokinetic Chromatography with Bile Salt Micelles," J. Chromatogr., vol. 480, pp. 403–411 (1989).

S. Terabe et al., "Separation of Enantiomers by Capillary Electrophoretic Techniques," J. Chromatogr. A, vol. 666, pp. 295–319 (1994).

T. Ward, "Chiral Media for Capillary Electrophoresis," Anal. Chem., vol. 66, pp. 632A–640A (1994).

M. Novotny et al., "Chiral Separation through Capillary Electromigration Methods," Anal. Chem., vol. 66, pp. 646A–655A (1994).

S. Terabe et al., "Electrokinetic Chromatography with Micellar Solution and Open–Tubular Capillary," Anal. Chem., vol. 57, pp. 834–841 (1985).

S. Terabe et al., "Electrokinetic Separations with Micellar Solutions and Open–Tubular Capillaries," Anal. Chem., vol. 56, pp. 111–113 (1984).

C. Paleos et al., "Comparative Studies between Monomeric and Polymeric Sodium 10–Undecenoate Micelles," J. Phys. Chem., vol. 87, pp. 251–254 (1983).

D. Tabor et al., "Some Factors in Solute Partitioning between Water and Micelles or Polymeric Micelle Analogues," Chromatogr., vol. 20, pp. 73–80 (1989).

S. Terabe et al., "Ion–Exchange Electrokinetic Chromatography with Polymer Ions for the Separation of Isomeric Ions Having Identical Electrophoretic Mobilities," Anal. Chem., vol. 62, pp. 650–652 (1990).

J. Fendler et al., "Polymerized Surfactant Aggregates: Characterization and Utilization," Acc. Chem. Res., vol. 17, pp. 3–8 (1984).

K. Nagai et al., "Polymerization of Micellized 1–O–3–(4–vinylphenyl)propyl–$\beta$–D–glucopyranose," Makromol. Chem., vol. 188, pp. 1095–1127 (1987).

J. Wang and I. Warner, "Chiral Separations Using Micellar Electrokinetic Capillary Chromatography and a Polymerized Chiral Micelle," Anal. Chem., vol. 66, pp. 3773–3776 (Nov. 1, 1994).

J. Wang and I. Warner, "Combined Polymerized Chiral Micelle and $\gamma$–Cyclodextrin for Chiral Separation in Capillary Electrophoresis," pp. 1–21 undated.

D. Armstrong et al., "Enrichment of Enantiomers and Other Isomers with Aqueous Liquid Membranes Containing Cyclodextrin Carriers," Anal. Chem., vol. 59, pp. 2237–2241 (1987).

K. Taguchi et al., "Immobilized Bilayer Stationary Phases in Gas Chromatography," J. Chem. Soc., Chem. Commun., pp. 364–365 (1986).

Y. Ishihama et al., "Enantiomeric Separation by Micellar Electrokinetic Chromatography Using Saponins," J. Liq. Chromatogr., vol. 16, pp. 933–944 (1993).

C. Larrabee et al., "Radiation–Induced Polymerization of Sodium 10–Undecenoate in Aqueous Micelle Solutions," J. Poly. Sci.: Poly. Lett. Ed., vol. 17, pp. 749–751 (1979).

C. Palmer et al., "A Monomolecular Pseudostationary Phase for Micellar Electrokinetic Capillary Chromatography," J. High Res. Chromatogr., vol. 15, pp. 756–762 (1992).

K. Otsuka et al., "Enantiomeric Resolution by Micellar Electrokinetic Chromatography with Chiral Surfactants," J. Chromatogr., vol. 515, pp. 221–226 (1990).

[Step 1]

(fatty acid)    (N-hydroxysuccinimide)    (dicyclohexylcarbodiimide)

(N-hydroxysuccinimide ester of fatty acid)    (dicyclohexylurea)

[Step 2]

(N-hydroxysuccinimide ester of fatty acid)    (sodium salt of amino acid)

(surfactant monomer)

[Step 3]

(surfactant monomer)    (polymerized chiral micelle)

POLYMERIZED CHIRAL MICELLES FOR CHIRAL SEPARATIONS

The development of this invention was funded by the Government under grant CHE 9224177 awarded by the National Science Foundation. The Government has certain rights in this invention.

The benefit of the Aug. 16, 1995 filing date of provisional application Ser. No. 60/029,184 is claimed under 35 U.S.C. § 119(e).

This invention pertains to methods and compositions useful in chiral separations of enantiomeric mixtures, particularly to the use of polymerized chiral micelles in such separations.

Chiral Separations

The separation of enantiomeric mixtures into individual optical isomers is one of the most challenging problems in analytical chemistry, reflecting practical considerations important in many areas of science, particularly the pharmaceutical and agricultural industries.

For example, the pharmaceutically active site of many drugs is "chiral," meaning that the active site is not identical to a mirror image of the site. However, many pharmaceutical formulations marketed today are racemic mixtures of the desired compound and its "mirror image." One optical form (or enantiomer) of a racemic mixture may be medicinally useful, while the other optical form may be inert or even harmful, as has been reported to be the case for thalidomide.

Chiral drugs are now extensively evaluated prior to large scale manufacturing, both to examine their efficacy, and to minimize undesirable effects attributable to one enantiomer or to the interaction of enantiomers in a racemic mixture. The United States Food and Drug Administration has recently issued new regulations governing the marketing of chiral drugs.

Separating optical isomers often requires considerable time, effort, and expense, even when state-of-the-art chiral separation techniques are used. There is a continuing and growing need for improved chiral separation techniques.

Early chiral separation methods used naturally occurring chiral species in otherwise standard separation protocols. For example, natural chiral polymeric adsorbents such as cellulose, other polysaccharides, and wool were used as early as the 1920's. Later strategies used other proteins and naturally occurring chiral materials. These early strategies gave some degree of success. However, the poor mechanical and chromatographic properties of naturally occurring materials often complicated the separations. Although naturally occurring chiral materials continue to be used for chiral separations, efforts have increasingly turned to synthesizing chiral materials having better mechanical and chromatographic properties. D. Armstrong, "Optical Isomer Separation by Liquid Chromatography," Anal. Chem., vol. 59, pp. 84A–91A (1987) gives a review of methods that have been used for chiral separations in liquid chromatography.

The two separation methods most often employed for chiral separations are high performance liquid chromatography and capillary electrophoresis, both of which have high efficiencies. High separation efficiencies are required for chiral separations because the difference in molar free energies of the interactions that discriminate between individual enantiomers is small, typically on the order of 100 calories per mole. The sum of the weighted time averages of these small interactions determines the overall enantioselectivity of a separation technique. High efficiencies are therefore important to improved chromatographic chiral separations. Separations on the order of 100,000 theoretical plates are readily achievable with capillary electrophoresis. Thus, small chiral selectivities can be magnified using capillary electrophoresis.

The so-called "three point rule" is a commonly used rule-of-thumb in many chiral recognition strategies. The "three point rule" recommends that there be a minimum of three simultaneous interactions between the chiral recognition medium and at least one of the enantiomers to be separated. In addition, at least one of the three interactions must be stereochemically dependent. The three interactions need not be attractive interactions, and may for example employ repulsion due to steric effects. For example, the "three point rule" was successfully used in 1971 in the design of a chiral stationary phase for the separation of the enantiomers of L-DOPA (L-dihydroxyphenylalanine). See R. J. Baczuk et al., "Liquid Chromatographic Resolution of Racemic β-3,4-Dihydroxyphenylalanine," J. Chromatogr., vol. 60, pp. 351–361 (1971).

Until recently, the most common type of synthetic chiral stationary phase used in high performance liquid chromatography ("HPLC") was a Pirkle-type (Brush-type) phase. A Pirkle-type phase is based on the "three point rule," and usually employs $\pi$—$\pi$ interactions (electron donor-acceptor) and intermolecular hydrogen bonding in chiral recognition.

Another successful approach has used reversible complexes formed of metal ions and chiral complexing agents. This separation method is commonly called ligand-exchange-chromatography ("LEC"). LEC is usually explained by a model based on multicomponent complexes containing a central metal ion and two chelating chiral molecules. Enantiomers can be separated in LEC either by using chiral mobile phase additives, or by using a chiral stationary phase.

Host-guest enantioselective complexes, in either the mobile phase or the stationary phase, can also be used to separate individual enantiomers. Systems within this general category include those employing chiral crown ethers and cyclodextrins. Compared to crown ethers, cyclodextrins are relatively inexpensive, and are more readily derivatized. See E. Gassmann et al., "Electrokinetic Separation of Chiral Compounds," Science, vol. 230, pp. 813–814 (1985); and R. Kuhn et al., "Chiral Separation by Capillary Electrophoresis," Chromatographia, vol. 34, pp. 505–512 (1992). For example, D. Armstrong et al., "Enrichment of Enantiomers and Other Isomers with Aqueous Liquid Membranes Containing Cyclodextrin Carriers," Anal. Chem., vol. 59, pp. 2237–2241 (1987) disclose the use of an aqueous liquid membrane employing cyclodextrin carriers to perform an enantiomeric enrichment.

Micelles

Surfactants, molecules having both hydrophilic and hydrophobic groups, associate with one another in polar solvents such as water to form dynamic aggregates known as "micelles." A micelle typically takes roughly the shape of a sphere, a spheroid, an ellipsoid, or a rod, with the hydrophilic groups on the exterior and the hydrophobic groups on the interior. The hydrophobic interior provides, in effect, a hydrophobic liquid phase with solvation properties differing from those of the surrounding solvent. Micelles form when the concentration of the amphophilic molecules in solution is greater than a characteristic value known as the critical micelle concentration ("CMC").

Micelles have been used for a variety of purposes, including micellar catalysis; micelle-substrate interactions; and analytical applications such as spectroscopic analyses, electrochemical measurements, and separations. For example, K. Taguchi et al., "Immobilized Bilayer Stationary Phases in Gas Chromatography," J. Chem. Soc., Chem. Commun., pp. 364–365 (1986) disclose the use of an immobilized, stable, poly-ion complex containing vesicles for use in a gas chromatography column.

For a general discussion of micellar electrokinetic capillary chromatography, see S. Terabe et al., "Electrokinetic Chromatography with Micellar Solution and Open-Tubular Capillary," Anal. Chem., vol. 57, pp. 834–841 (1985); and S. Terabe et al., "Electrokinetic Separations with Micellar Solutions and Open-Tubular Capillaries," Anal. Chem., vol. 56, pp. 111–113 (1984).

Chiral Micelles

An important application of micelles is their use in chiral recognition and separation. Chiral surfactants have been used to form micelles having distinct chiral properties. The resulting chiral microenvironment has been shown to exhibit selective interactions with different enantiomers in solution. See, e.g., S. Terabe et al., "Chiral Separation by Electrokinetic Chromatography with Bile Salt Micelles," J. Chromatogr., vol. 480, pp. 403–411 (1989); S. Terabe et al., "Separation of Enantiomers by Capillary Electrophoretic Techniques," J. Chromatogr. A, vol. 666, pp. 295–319 (1994); T. Ward, "Chiral Media for Capillary Electrophoresis," Anal. Chem., vol. 66, pp. 632A–640A (1994); and M. Novotny et al., "Chiral Separation through Capillary Electromigration Methods," Anal. Chem., vol. 66, pp. 646A–655A (1994).

In addition to the equilibrium between micelles and ligands, there is also a dynamic equilibrium between surfactant molecules and micelles. "Conventional" micelles are dynamic aggregates of surfactant monomers; the monomers exist in equilibrium between aggregation in micelles, and being free in solution as smaller aggregates down to monomers. Because the difference in interactions between a chiral micelle and two enantiomers is often very small, these dynamic equilibria may interfere with the separation of enantiomers. See the schematic diagram of FIG. 9(a), in which an asterisk represents a chiral center, and S represents the solute.

Mixed chiral micelle systems have been reported to have enhanced resolving power as compared to the resolving power of micelles formed from the individual components. See K. Otsuka et al., "Enantiomeric Resolution by Micellar Electrokinetic Chromatography with Chiral Surfactants," J. Chromatogr., vol. 515, pp. 221–226 (1990); and Y. Ishihama et al., "Enantiomeric Separation by Micellar Electrokinetic Chromatography Using Saponins," J. Liq. Chromatogr., vol. 16, pp. 933–944 (1993).

Polymerized Micelles

Polymerized surfactant aggregates, or polymerized micelles, were first developed in the late 1970's and early 1980's. Compared to otherwise identical non-polymerized micelles ("conventional micelles"), polymerized micelles exhibit enhanced stability, enhanced rigidity, and better control over micelle size. The covalent bonds between surfactant monomers essentially eliminate the dynamic equilibrium between surfactant monomers and "conventional" micelles, simplifying and enhancing complexation between micelle and ligand.

An important advantage of polymerized micelles is that they have no critical micelle concentration ("CMC"). Because the individual surfactant monomers in a polymerized micelle must associate with one other, micelles form regardless of how low their concentration is. By contrast, with non-polymerized micelles the concentration of the surfactant must be higher than the CMC for a significant concentration of micelles to form. Furthermore, if the CMC of a charged surfactant is high, the high concentration of surfactant will generate considerable heat in micellar electrokinetic capillary chromatography (MECC), due to the high current resulting from the high charge density in solution. The heat generated can be deleterious to separations. By contrast, generation of heat with polymerized micelles can be greatly reduced because polymerized micelles have no CMC.

C. Palmer et al., "A Monomolecular Pseudostationary Phase for Micellar Electrokinetic Capillary Chromatography," J. High Res. Chromatogr., vol. 15, pp. 756–762 (1992) discloses the use of an oligomerized sodium 10-undecylate micelle-like structure in micellar electrokinetic capillary chromatography. See also C. Larrabee et al., "Radiation-Induced Polymerization of Sodium 10-Undecenoate in Aqueous Micelle Solutions," J. Poly. Sci.: Poly. Lett. Ed., vol. 17, pp. 749–751 (1979).

Polymerized micelles are typically more rigid than conventional micelles, a property that may result in faster mass transfer. Polymerized micelles have a more compact structure than do conventional micelles. Thus solute molecules do not penetrate as deeply, which may result in faster mass transfer rates. See C. Paleos et al., "Comparative Studies between Monomeric and Polymeric Sodium 10-Undecenoate Micelles," J. Phys. Chem., vol. 87, pp. 251–254 (1983).

For other disclosures of polymerized micelles and their uses in separations, see also D. Tabor et al., "Some Factors in Solute Partitioning between Water and Micelles or Polymeric Micelle Analogues," Chromatogr., vol. 20, pp. 73–80 (1989); S. Terabe et al., "Ion-Exchange Electrokinetic Chromatography with Polymer Ions for the Separation of Isomeric Ions Having Identical Electrophoretic Mobilities," Anal. Chem., vol. 62, pp. 650–652 (1990); J. Fendler et al., "Polymerized Surfactant Aggregates: Characterization and Utilization," Acc. Chem. Res., vol. 17, pp. 3–8 (1984); and C. Palmer et al., "A Monomolecular Pseudostationary Phase for Micellar Electrokinetic Capillary Chromatography," J. High Res. Chromatogr., vol. 15, pp. 756–762 (1992).

See also K. Nagai et al., "Polymerization of Micellized 1-O-3-(4-vinylphenyl)propyl-β-D-glucopyranose," Makromol. Chem., vol. 188, pp. 1095–1127 (1987), disclosing the preparation of a polymerized micelle from the monomer 1-O-3-(4-vinylphenyl)propyl-β-D-glucopyranose. Although the monomer is chiral, nothing in the Nagai et al. paper mentions chirality. The paper describes the polymer as if it were a conventional polymerized micelle. The focus of the paper was to contrast the properties of polymerized and non-polymerized micelles. That the starting monomer may have been chiral appears to have been no more than coincidence. The Nagai et al. paper does not disclose whether the polymer retained any optical activity, nor does it suggest that the polymer might have any application in chiral separations. Indeed, the paper does not refer to chirality in any context. With this single exception, to the knowledge of the inventors all previously-reported polymerized micelles have been achiral.

Novel Chiral Separations using Polymerized Chiral Micelles

It has been discovered that chiral separations can be enhanced through the use of polymerized chiral micelles. Because polymerized micelles eliminate much of the complex dynamic behavior otherwise associated with micelles, polymerized chiral micelles have stronger chiral recognition properties than do otherwise-identical, "conventional" or non-polymerized chiral micelles. See the schematic diagram of FIG. 9(b).

In addition, recovery of chiral ligands from polymerized chiral micelles is often far easier; the chiral ligands may typically be recovered by simple extraction with an appropriate organic solvent. By contrast, recovering the solute from a conventional, non-polymerized micellar medium by extraction with an organic solvent frequently causes the formation of troublesome emulsion systems. Polymerized chiral micelle systems are therefore beneficial in both preparative-scale and process-scale separations.

EXAMPLES 1 AND 2

As embodiments of this invention, we have synthesized two novel polymerized chiral micelles: poly (sodium N-undecylenyl-L-valinate) (poly (L-SUV)) and poly (sodium N-undecylenyl-D-valinate) (poly (D-SUV)). These molecules were prepared via the general synthetic scheme illustrated in FIG. 1 (discussed in greater detail below). After γ-irradiation with a cobalt-60 source to promote polymerization, the compounds were purified by lyophilization, followed by dissolution with ethanol to remove unreacted monomer. The product was then dried under vacuum. Table I lists some properties of these two polymers.

TABLE I

Properties of L-SUV and D-SUV Polymer Micelles

| | Optical Rotation $[\alpha]^{25}_D$ (c = 1, H$_2$O) | Hydrodynamic Radius of Polymer Micelle |
|---|---|---|
| Poly (L-SUV) | −8° | ~20Å |
| Poly (D-SUV) | +8° | ~20Å |

The hydrodynamic radii of the polymer micelles reported in Table I were measured by standard light scattering techniques. The values given represent the smallest polymers formed in aqueous solutions. The measured values for the radius were close to the lower limit of the instrument's measurement capability, and should therefore be considered approximate. Larger aggregates were also noted in the solution, a feature that is common in micellar solutions.

To further characterize the properties of the polymerized micelles and the corresponding surfactant monomers, fluorescence quenching was used to measure both the aggregation number of the "conventional" micelle formed by surfactant monomers, and the degree of polymerization of the polymerized micelles. The measured aggregation number for "conventional" micelles was approximately 60. Interestingly, within experimental error the mean number of monomers per polymerized micelle was the same, corresponding to a molecular weight of about 18,000. These results suggest that polymerization occurred primarily within micelles. Thus the size of polymerized micelles is controllable. The size of the polymer may be changed, if desired, by manipulating the aggregation number of the corresponding "conventional" micelles through means known in the art, prior to polymerization. For example, the aggregation number may be changed by altering the length of the surfactant molecules, by altering the hydrophobicity of the surfactant, or by adding an organic solvent to the surfactant solution.

EXAMPLES 3–5

Figure 2A:
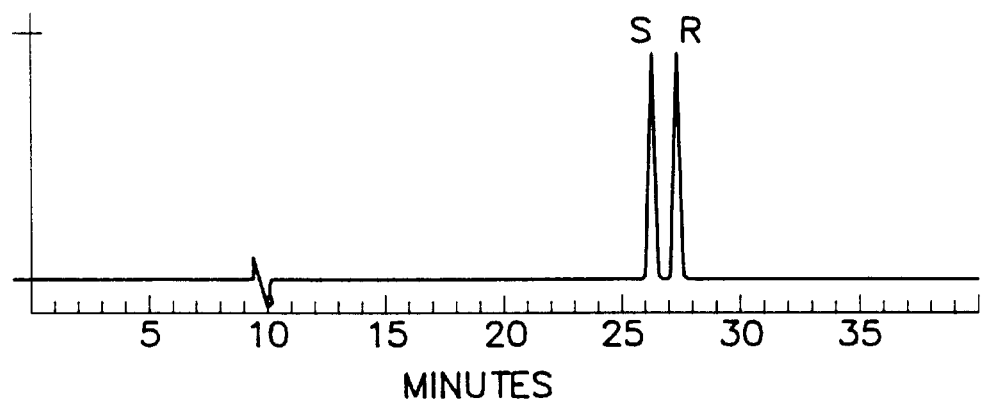
FIG. 2(a) illustrates the electrophoretic separation of a racemic mixture of (±)-1,1'-bi-2-naphthol with 0.5% (w/v) poly (L-SUV).

The baseline electrophoretic separation of a racemic mixture of (±)-1,1'-bi-2-naphthol with 25 mM sodium borate buffer (pH 9.0) containing 0.5% (w/v) poly (L-SUV) is illustrated in FIG. 2(a). These data demonstrate the chiral recognition ability of the polymerized micelle. The S-(−)-1,1'-bi-2-naphthol enantiomer eluted faster than did the corresponding R form. This suggests that R-(+)-1,1'-bi-2-naphthol has a higher affinity for the S (L) form of the chiral polymer. As was then expected, when poly (D-SUV) was substituted for poly (L-SUV), the elution order of the enantiomers of (±)-1,1'-bi-2-naphthol was reversed (data not shown).

Figure 2B:
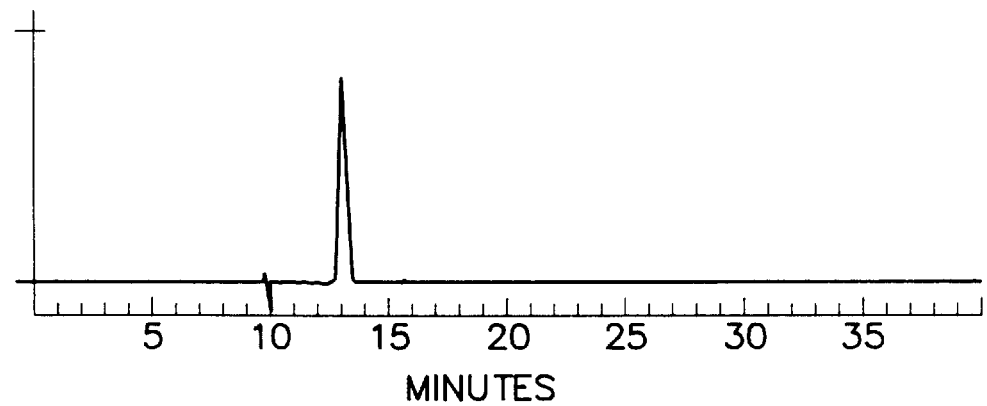
FIGS. 2(b) and 2(c) illustrate otherwise identical separations, except that the surfactant used was the non-polymerized L-SUV surfactant at concentrations of 0.5% (w/v) and 1% (w/v), respectively.
Figure 2C:
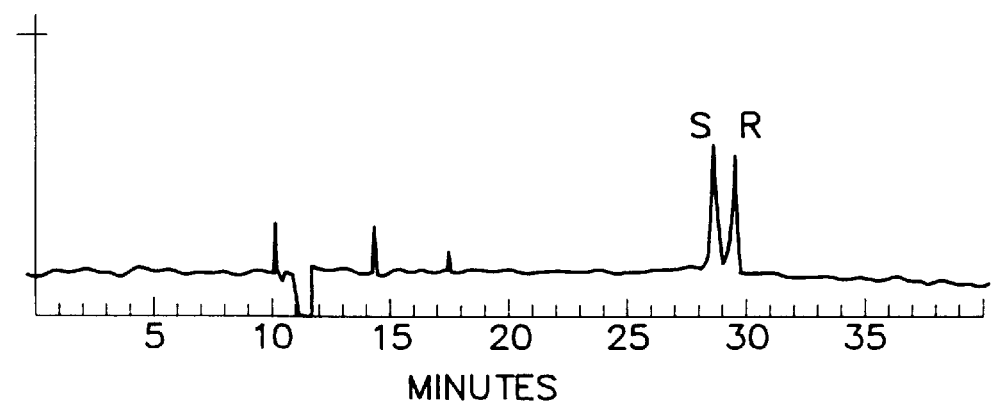

FIGS. 2(b) and 2(c) illustrate results from experiments that were otherwise identical, except that the non-polymerized L-SUV surfactant was used at concentrations of 0.5% (w/v) and 1% (w/v), respectively. No separation was noted at a surfactant concentration of 0.5%, a concentration just below the critical micelle concentration of the non-polymerized surfactant. Chiral separation was noted only when the surfactant concentration was increased to 1%, but even at this higher concentration the separation was not as sharp as that obtained with the polymerized micelle.

In the experiments of each of FIGS. 2(a), 2(b), and 2(c), the following electrophoresis conditions were used: buffer, 25 mM borate buffer (pH 9.0); applied voltage, 12 KV; and UV detection at 290 nm. In the experiment reported in FIG. 2(a), the measured electrophoretic current was 39 μA; in FIG. 2(b), 40 μA; and in FIG. 2(c), 51 μA.

EXAMPLES 6 AND 7

Figure 3A:
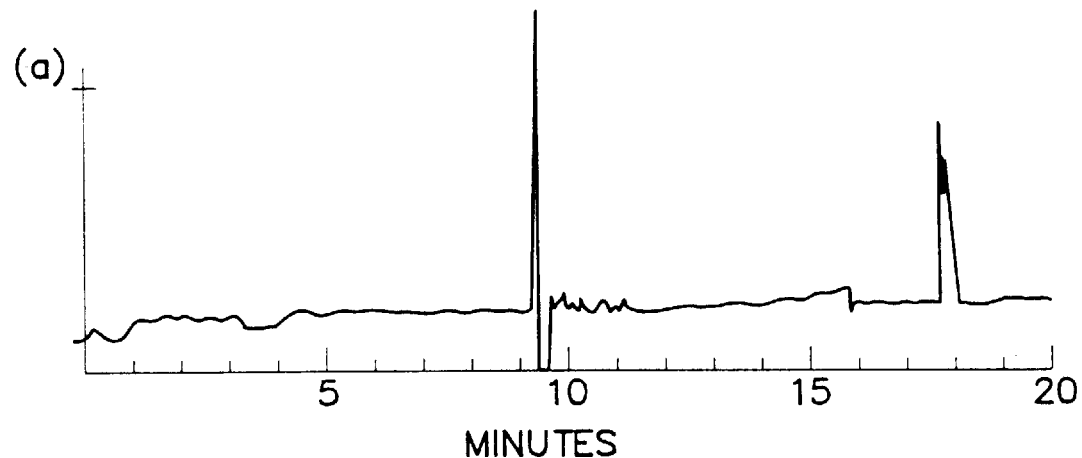
FIGS. 3(a) and 3(b) illustrate the effect of pH on the poly (L-SUV) resolution of the enantiomers D,L-laudanosine.
Figure 3B:
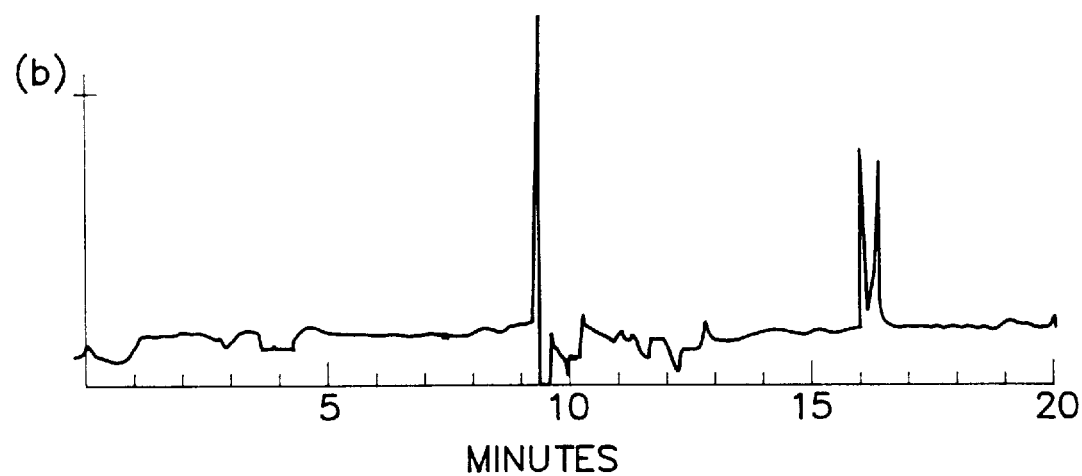

We have also used poly (L-SUV) to resolve a second pair of enantiomers—D,L-laudanosine. In this separation, the pH of the buffer played an important role. As illustrated in FIG. 3(a), only slight resolution was achieved at pH 9.0. However, at pH 10.0 (adjusted with NaOH) there was a near-baseline separation (Rs=1.2)—See FIG. 3(b). Detection was by UV at 254 nm. Other conditions were as reported above for the experiments reported in FIG. 2. At lower pH, the negatively charged polymerized micelles have a more compact conformation, while at higher pH, the negatively charged poly (L-SUV) micelles tend to have a more expanded conformation due to electrostatic repulsion. The expanded conformation can permit a higher degree of interaction with the ligands.

EXAMPLES 8–11

In another embodiment of this invention a combination of the polymerized chiral micelle poly (D-SUV) and γ-cyclodextrin (γ-CD) was used in an enhanced chiral separation via capillary electrophoresis. Mixtures of four enantiomeric pairs were successfully resolved with this combination. The resolutions of the enantiomer separations were superior to the resolutions obtained with either poly (D-SUV) alone or with γ-CD alone.

Cyclodextrins (CD's) are cyclic oligosaccharides with a 1–4 linkage of D-(+)-glucopyranoside units. CD's have been used as chiral selectors in chromatographic techniques and in capillary electrophoresis ("CE") because of their ability to form selective molecular inclusion complexes with a variety of organic species, both neutral and charged. The toroidal shape of CD's, and the five chiral centers of each glucose subunit are advantageous in chiral separations. However, CD's are neutral compounds, and in CE migrate only with the electroosmotic flow (EOF), limiting their separation ability. Ionic derivatives of CD's and CD-MECC have therefore usually been used in chiral separations.

The CD-MECC technique combines CD's and micellar systems in the same buffer. In the past, this combination suffered from an inherent interference that tends to reduce chiral resolution, namely that the surfactant monomers will complex with the CD's.

Polymerized chiral micelles have an enhanced stability that can be advantageously used in CD-MECC to reduce the degree of complexation otherwise observed between surfactant monomers and CD's. Furthermore, because polymerized micelles have no CMC, they may be used in MECC over a wider range of concentrations.

Combinations of both poly (L-SUV) and the antipode poly (D-SUV) with γ-CD were tested in four chiral separations. The separations of mixtures of four enantiomeric pairs with the combination of poly (D-SUV) and γ-CD were superior to the separations obtained by using either poly (D-SUV) or γ-CD separately. Without wishing to be bound by this theory, the polymerized chiral micelle may be considered to behave as a pseudo-stationary phase, while the neutral γ-CD may be considered to be found primarily in the aqueous phase.

(±)-1,1'-Bi-2-naphthol (99%), (R)-(+)-1,1'-bi-2-naphthol (99%), S-(−)-1,1'-bi-2-naphthol (99%), (±)-1,1'-binaphthyl-2,2'-diyl hydrogenphosphate (BNPO$_4$) (99%), and (±)-verapamil (95%) were purchased from Aldrich (Milwaukee, Wis.). D,L-laudanosine (95%), L-valine (>99%), D-valine (99%) and undecylenic acid (>99%) were obtained from Sigma (St. Louis, Mo.). The γ-cyclodextrin was a gift from American Maize Products (Hammond, Ind.). (γ-cyclodextrin is a particular cyclodextrin structure.) Each of these compounds was used as received.

Micellar electrokinetic capillary chromatography was conducted with a CES I capillary electrophoresis system (Dionex Co., Sunnyvale, Calif.). Data were collected with an Al-450 chromatography workstation. The separation column was an untreated fused silica capillary (effective length 60 cm, 75 mm i.d.) from Polymicro Technologies (Phoenix, Ariz.). The solution was buffered at pH 9 with borate buffer. The polymerized micelles and γ-CD were added directly to the buffer system. The buffer solutions were filtered through a 0.45 mm membrane filter prior to use. Separations were performed at 12 kV with UV detection at 280 nm. Samples were prepared in a 10:90 methanol:water mixture in a concentration range from 0.02 to 0.1 mg/mL.

FIG. 4 illustrates the advantages of an enantiomeric separation using a combination of γ-CD and poly (D-SUV). When γ-CD only was used (10 mM), R-1,1'-bi-2-naphthol had a higher affinity for γ-CD, and migrated faster than the (S) form (FIG. 4(a)). When poly (D-SUV) only was used (0.5%), the S-1,1'-bi-2-naphthol interacted more strongly with the polymer than did the (R) form, and R-1,1'-bi-2-naphthol again migrated through the system faster than the (S) form (FIG. 4(b)). But when the two chiral selectors were used together at the same concentrations, the combined effects of γ-CD and poly (D-SUV) resulted in significantly greater chiral resolution than obtained with either alone (FIG. 4(c)).

Figure 4A:
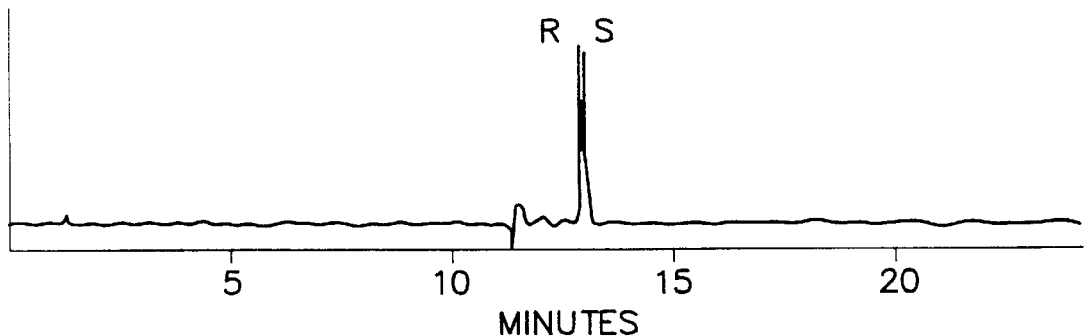
FIG. 4(a) illustrates the separation of R,S-1,1'-bi-2-naphthol with γ-CD only.
Figure 4B:
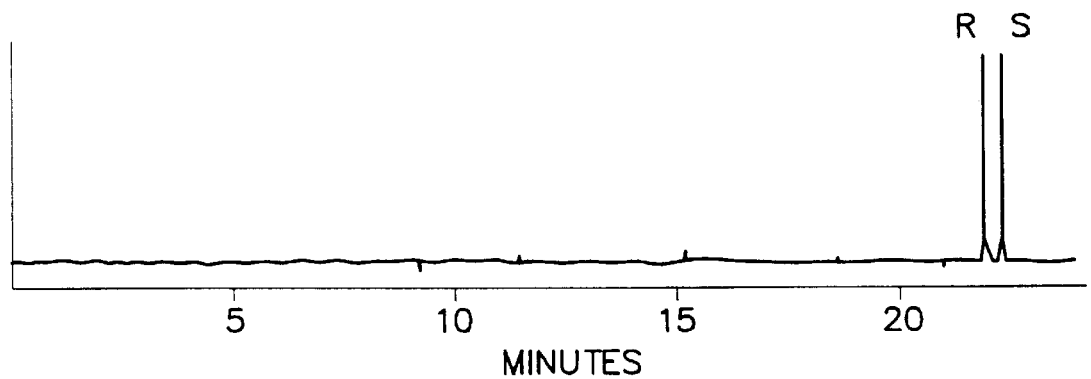
FIG. 4(b) illustrates the same separation when poly (D-SUV) only was used.
Figure 4C:
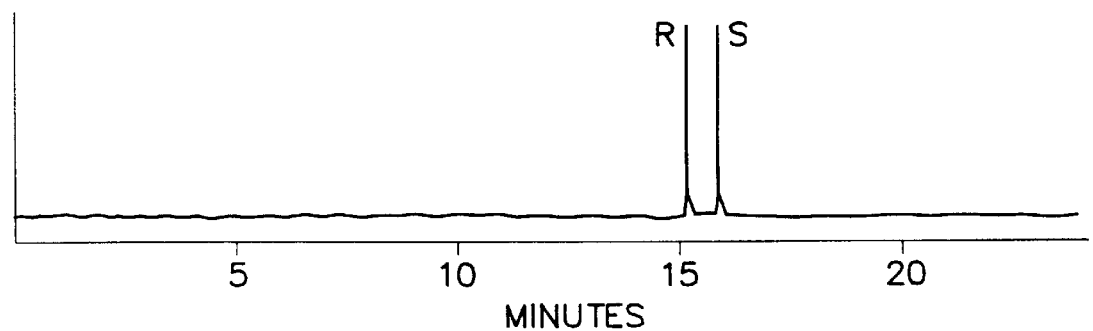
FIG. 4(c) illustrates the same separation when γ-CD and poly (D-SUV) were used together.
Figure 4D:
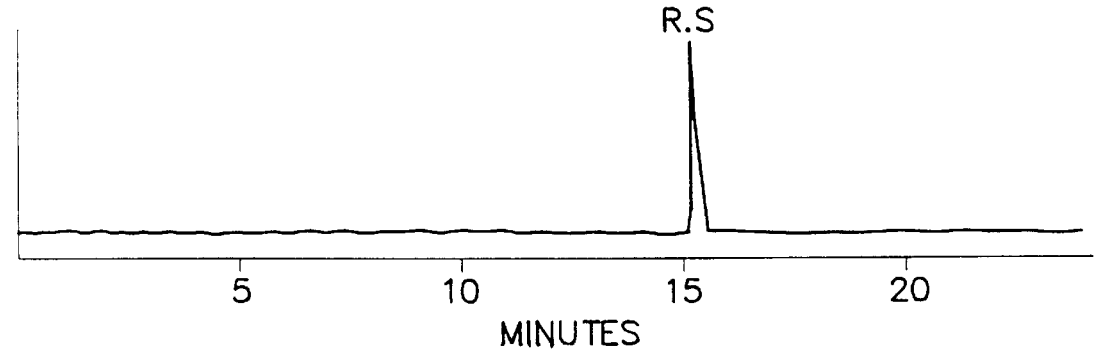
FIG. 4(d) illustrates the same separation when γ-CD was instead combined with the antipode poly (L-SUV).
Figure 5A:
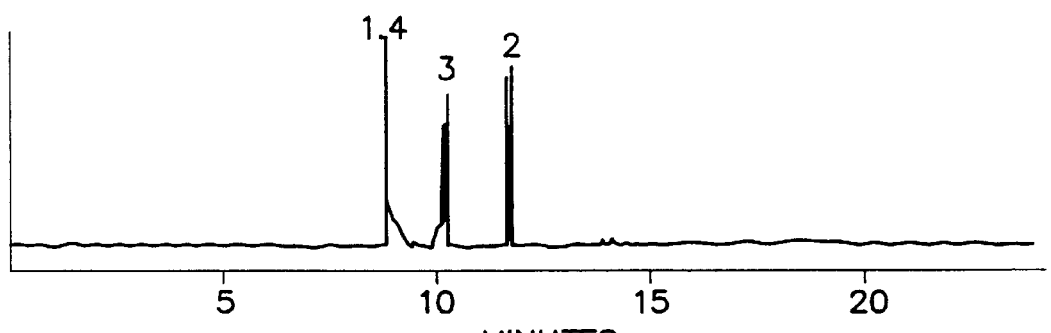
FIG. 5 illustrates separations of mixtures of four pairs of enantiomeric compounds: R,S-verapamil; R,S-1,1'-binaphthyl-2,2'-diyl hydrogen phosphate; R,S-laudanosine; and R,S-1,1'-bi-2-naphthol; using γ-CD alone (FIG. 5(a)), using poly (D-SUV) alone (FIG. 5(b)), using both γ-CD and poly (D-SUV) (FIG. 5(c)), and using both γ-CD and poly (D-SUV) under optimized conditions (FIG. 5(d)).
Figure 5B:
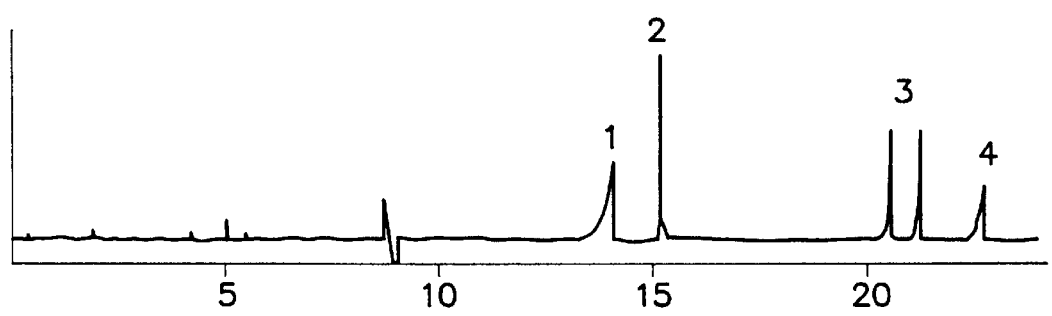
Figure 5C:
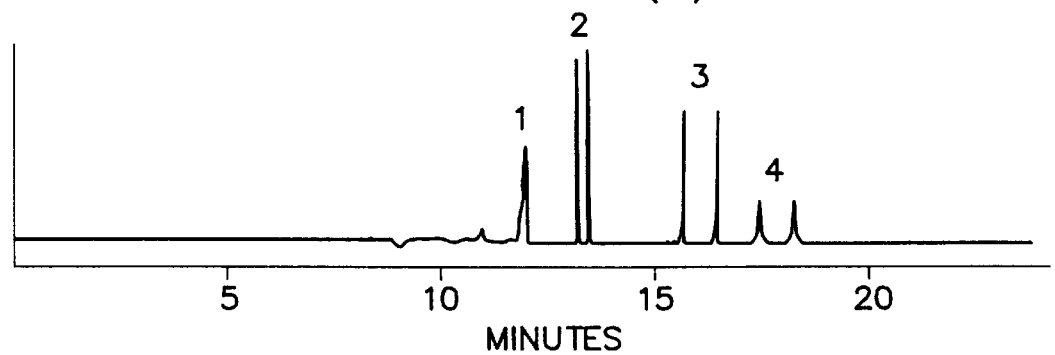
Figure 5D:
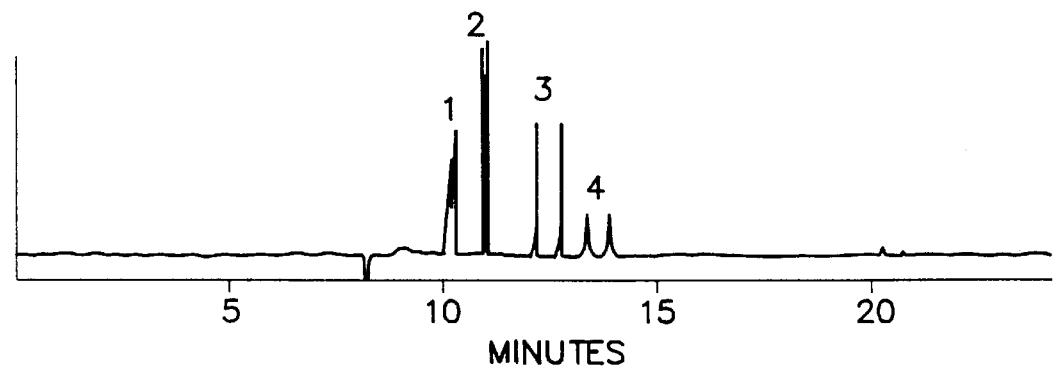

By contrast, as shown in FIG. 4(d), when γ-CD was combined with the antipode poly (L-SUV) at the same concentrations, chiral resolution was diminished because the effects of the two chiral components worked against one another.

EXAMPLES 12–15

FIG. 5 shows separations of mixtures of four pairs of enantiomeric compounds, again with 10 mM concentrations of γ-CD (where used), and 0.5% concentration of the polymerized micelle (where used): R,S-laudanosine (collectively labelled 1 in the Figure); R,S-1,1'-binaphthyl-2,2'-diyl hydrogen phosphate (labelled 2); R,S-1,1'-bi-2-naphthol (labelled 3); and R,S-verapamil (labelled 4 in the Figure). Using either γ-CD alone or poly (D-SUV) alone at the concentrations examined, satisfactory resolution was not achieved (FIGS. 5(a) and 5(b), respectively). However, using both γ-CD and poly (D-SUV) at the same concentrations resolved three enantiomeric pairs (FIG. 5(c)). Each of the experiments reported in FIGS. 5(a), 5(b), and 5(c) used 25 mM borate buffer at pH 9. With 5 mM pH 9 borate buffer instead, all four compounds were resolved (FIG. 5(d)).

Because several factors can influence chiral separations, some straightforward experiments were conducted to optimize this CD-Chiral MECC system.

EXAMPLES 16–19

Effect of γ-CD Concentration on Enantiomeric Resolution

Figure 6:
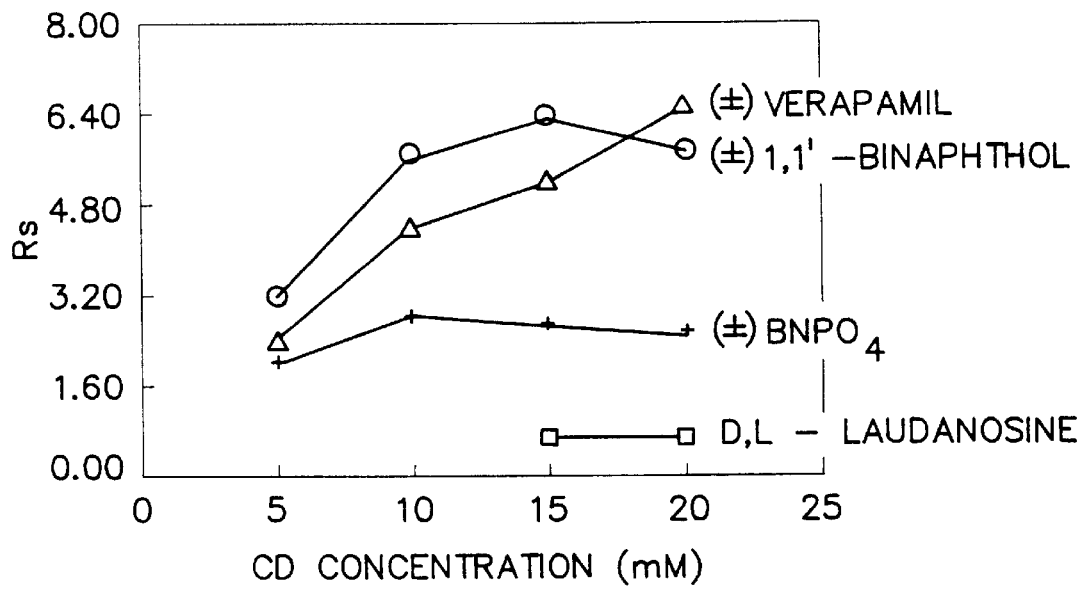
FIG. 6 illustrates the effect of CD concentration on the resolution of four pairs of enantiomeric compounds.

The effect of γ-CD concentration on the separations was investigated over the concentration range 5–20 mM. FIG. 6 shows the effect of CD concentration on the resolution of four pairs of enantiomeric compounds. In each case, 0.5% poly (D-SUV) was used, with 25 mM pH 9 borate buffer. Resolution was observed generally to increase with increasing cyclodextrin concentration, until a maximum was reached. Further increases in CD concentration then caused a decrease in resolution. The optimum concentration of cyclodextrin depended on the particular enantiomeric pair being separated. The optimum CD concentration for (±)-BNPO$_4$ was approximately 10 mM; for (±)-1,1'-bi-2-naphthol, approximately 15 mM; for (±)-verapamil, above 20 mM. For D,L-laudanosine, an increase in γ-CD concentration initially improved enantiomeric separation, but further increases did not significantly change the resolution. This observation suggests that the interactions between D,L-laudanosine enantiomers and γ-CD are weak, and that the resolution of this enantiomeric pair cannot be improved significantly by the addition of γ-CD alone.

EXAMPLES 20–23

Effect of Buffer Concentration on Enantiomeric Resolution

Figure 7:
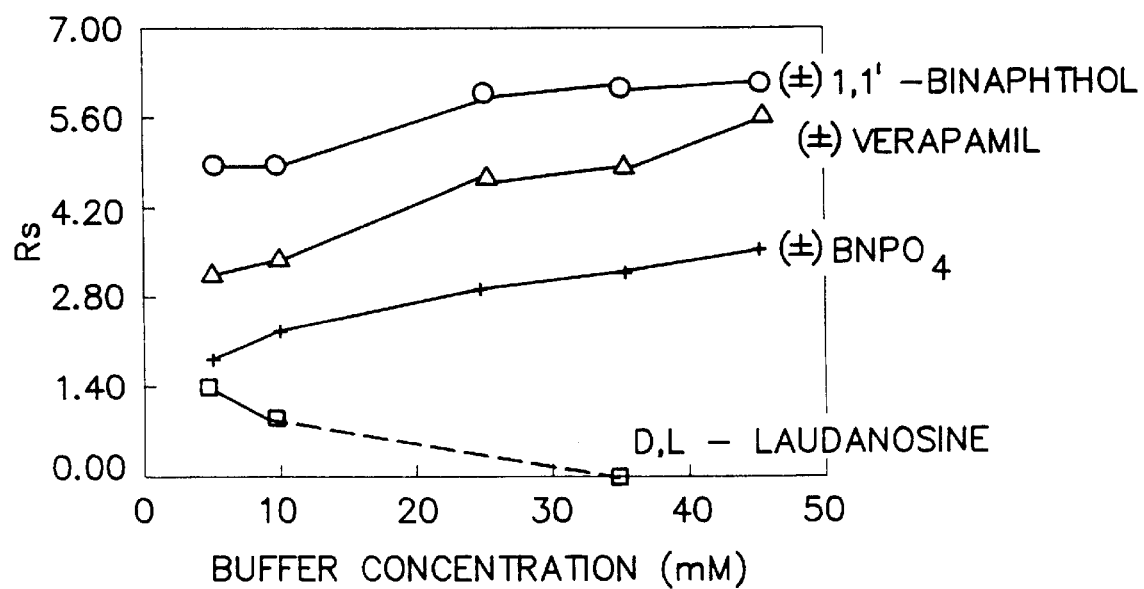
FIG. 7 illustrates the effect of borate buffer concentration on the resolutions of enantiomeric pairs.

The buffer concentration determined the ionic strength of the electrolyte. Increasing the buffer concentration reduced the EOF, and also increased the viscosity of the electrolyte. These effects both expand the migration time window for the CD-MECC system. This expansion usually, but not always, resulted in increased chiral resolution. In the chiral separations tested, increasing the borate buffer concentration from 5 mM to 45 mM lengthened the migration time for each compound. The resolutions of most enantiomeric pairs were enhanced, except that the resolution for D,L-laudanosine decreased (FIG. 7). In each case, the following conditions were used: 0.5% poly (D-SUV), 10 mM γ-CD, and pH 9 borate buffer.

The charged polymer should be more flexible at lower buffer concentration than at higher buffer concentration.

This effect may have induced a larger difference in affinities between the polymer and the D-laudanosine and L-laudanosine enantiomers at the lower buffer concentration, resulting in higher resolution for that particular separation.

EXAMPLES 24–31

Effect of Organic Solvents on Enantiomeric Resolution

The effects of organic solvent modifiers on chiral resolution depend not only on the type of chiral selectors used, but also on the properties of the enantiomers, e.g. their hydrophobic and hydrophilic properties. In general, the migration time of the samples increased with an increase in the concentration of organic solvents, due to a decrease in the EOF. In "conventional" MECC or CD-MECC, if the concentration of an organic solvent such as methanol is sufficiently high, the micelle decomposes into surfactant monomers so that solute-micelle interaction is not possible.

Figure 8:
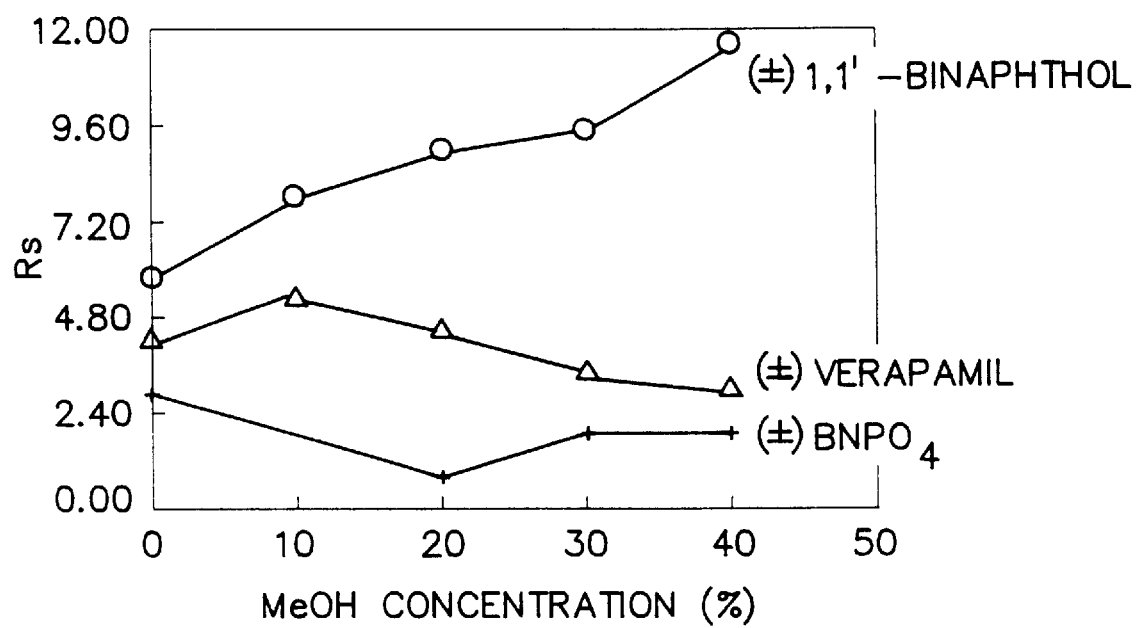
FIG. 8 illustrates the effect of methanol concentration on the resolutions of enantiomeric pairs.
Figure 9A:
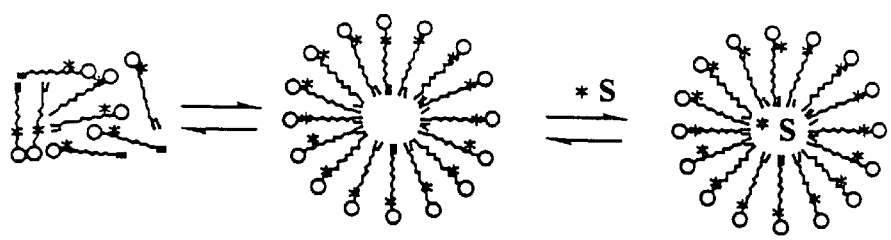
FIGS. 9(a) and 9(b) illustrate schematically the dynamic interactions associated with "conventional" chiral micelles and polymerized chiral micelles, respectively.
Figure 9B:
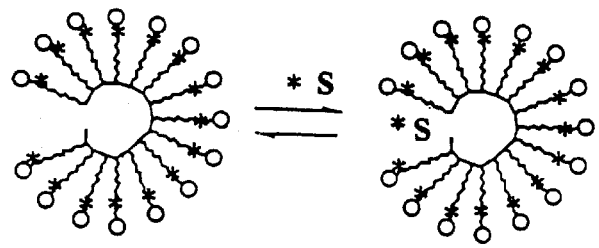

By contrast, even at very high concentrations of methanol in the novel system (e.g., 40%), the enantiomeric resolutions of the compounds examined were still very good, except that for D,L-laudanosine (FIG. 8). Even a small amount of methanol impaired the separation of D,L-laudanosine. In each case, the following conditions were used: 0.5% poly (D-SUV), 25 mM pH 9 borate buffer, 10 mM γ-CD.

Note in FIG. 8 that the remaining three enantiomeric pairs behaved differently at different methanol concentrations. Consider, for example, the enantiomeric resolution of (±)-1,1'-bi-2-naphthol as a function of methanol concentration. When only poly (D-SUV) was used (data not shown), the resolution of (±)-1,1'-bi-2-naphthol increased at higher methanol concentrations. But when only γ-CD was used (data not shown), the resolution decreased slightly as methanol concentration increased. When a combination of both was used (FIG. 8), there was a net resolution increase upon addition of methanol.

Enantiomeric resolution of (±)-verapamil increased with increasing methanol concentration up to 10%. However, above 10% methanol, the resolution decreased upon further increases in methanol concentration.

By contrast, the enantioselectivity of (±)-BNPO$_4$ decreased with increasing methanol concentration up to 10%. But at higher methanol concentrations, the resolution increased again. The best resolution was still obtained in aqueous buffer without methanol.

EXAMPLE 32

Synthesis of a Polymerized Chiral Micelle

Figure 1:
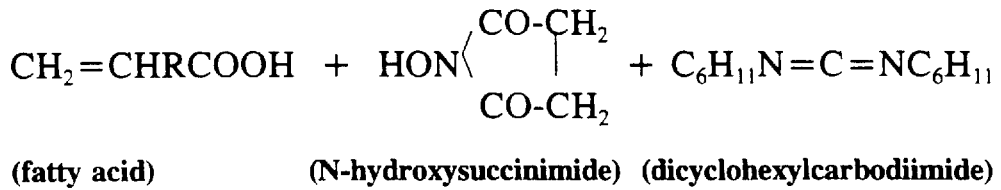
FIG. 1 illustrates the synthetic scheme that was used in making a polymerized chiral micelle embodiment of the present invention.
Figure 1:
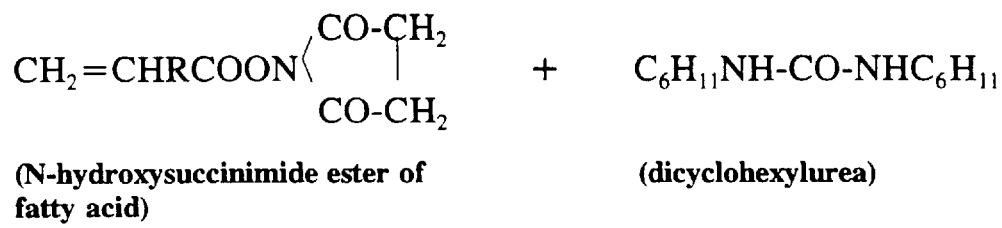
Figure 1:
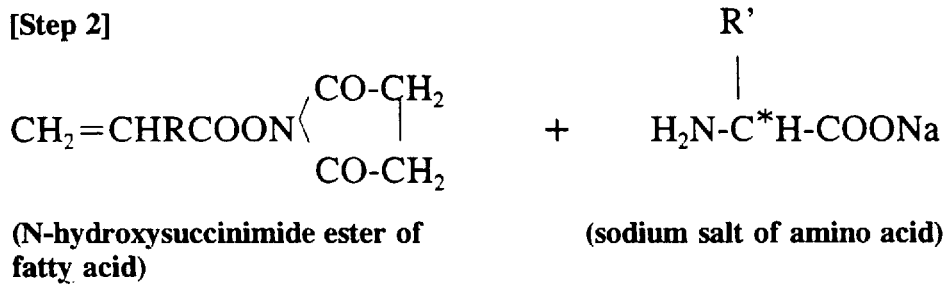
Figure 1:
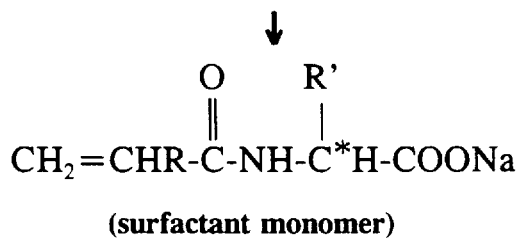
Figure 1:
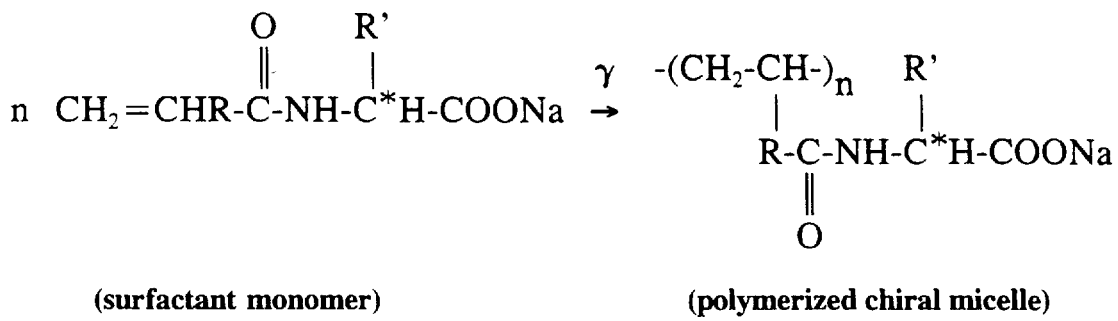

The scheme used for synthesizing poly (sodium undecylenyl L-valinate) is given below, and is illustrated in FIG. 1, in which an asterisk denotes a chiral center.

Step 1

Synthesis of N-hydroxysuccinimide ester 1. 100 mmols of undecylenic acid and 100 mmols N-hydroxysuccinimide were dissolved in about 500 mL dry ethyl acetate.

2. 100 mmols of dicyclohexylcarbodiimide, dissolved in 30 mL dry ethyl acetate, were added to the mixture and stirred overnight (about 12 hours).

3. The reaction was terminated by filtering the reaction mixture and evaporating the ethyl acetate from the filtrate. A crude, white, waxy solid product was obtained.

4. The product was recrystallized from ethanol. A fine, leafy ester product was obtained.

Step 2

Synthesis of sodium undecylenyl L-valinate (L-SUV)

1. 20 mmols of sodium bicarbonate and 20 mmols of L-valine were dissolved in 150 mL of water.

2. 20 mmols of N-hydroxysuccinimide ester dissolved in 150 mL tetrahydrofuran (THF) were added to the mixture and stirred overnight.

3. The mixture was filtered, and the pH was adjusted to 2.0 with 1N HCl (converting the sodium surfactant to acid form, to remove inorganic impurities.)

4. The organic solvent (THF) was evaporated, and a white solid product was obtained.

5. The crude product was recrystallized by dissolution in chloroform, followed by the addition of petroleum ether until crystals began to form.

6. The acid form was converted to the sodium salt by adding equal moles of NaOH in a 1:1 v/v ethanol:H$_2$O solvent mixture.

7. The solvent was evaporated, and the sample was freeze-dried to obtain L-SUV.

The CMC of the synthesized non-polymerized L-SUV was determined by surface tension measurements to be $2.1 \times 10^{-2}$M.

Step 3

Polymerization of L-SUV

1. A 0.05M surfactant monomer solution was irradiated by $^{60}$Co (87 krad/hr) for more than 36 hours (total dose approximately 3–4 Mrad) to induce polymerization. While radiation is preferred because of its simplicity, other means known in the art may also be used to polymerize the monomers, such as using peroxide or other free radical initiators, or using UV irradiation instead of gamma-irradiation. See, for example, K. Nagai et al., "Polymerization of Micellized 1-O-3-(4-vinylphenyl)propyl-β-D-glucopyranose," Makromol. Chem., vol. 188, pp. 1095–1127 (1987).

2. After irradiation, the solution was lyophilized, and then washed with ethanol. The product was redissolved in H$_2$O, and dialyzed against bulk H$_2$O (MW cutoff: 1000).

3. The final product (the polymer) was dried under vacuum.

Proton NMR of the purified product did not show the multiplets of double bond proton signals present in the monomers, verifying polymerization. More importantly, NMR and FT-IR data indicated that key functional groups associated with the surfactant monomers remained intact in the polymerized micelles, and that the chirality of the micelles was not destroyed ($[\alpha]^{25}_D = -8.19°$, (c=1.00 in water)). The polymer was found to be 99% pure as calculated from elemental analysis.

Chiral micelle polymers in accordance with the present invention may be used as mobile phase additives for chiral separations in capillary electrophoresis, or in micellar liquid chromatography under reversed phase conditions. Our method of preparing chiral micelle polymers is easy to implement, and readily lends itself to use with a variety of polymers having different structures and degrees of chirality, which can be manipulated to enhance the chiral separations for particular analytes. Using synthetic means known in the art, the chiral centers can be moved to different locations along the individual monomers, and the number of chiral centers per micelle can be increased or decreased by using micelles with higher or lower aggregation numbers, respectively. Different monomer lengths may readily be generated through means known in the art. Fatty acid-type monomers terminating in double bonds are preferred, because such monomers may be used in the synthetic scheme described above with minimal modifications to the synthesis.

Different, or mixed polymerized chiral micelles could be used in a separation, which can result in enhanced separation where the different micelles have complementary separation properties. For example, a poly (sodium N-undecylenyl valinate) micelle could be placed in solution with a poly (sodium N-undecylenyl phenylalanate) to take advantage of the different properties of their different resolving properties.

Alternatively, different chiral surfactant monomers may be copolymerized. Copolymers frequently have properties differing from those of either corresponding homopolymer. For example, a surfactant monomer incorporating L-valine could be combined with one incorporating L-phenylalanine to form a mixed micelle. A polymerized micelle formed from this system would have chiral recognition properties similar to those of poly (L-SUV), in addition to the π-interaction chiral recognition properties of phenylalanine.

The synthetic scheme outlined above is a fairly general one in which the final steps may be modified to obtain a surfactant monomer with a different chiral center. For example, if π—π interaction is desired at the chiral center, phenylalanine, tyrosine, or tryptophan could be used in place of valine in the monomer synthesis. Histidine could also be used where a π—π interaction is desired, with care taken to "protect" one of the two amino groups of the histidine ring during synthesis.

In general, any unsaturated fatty acid may be substituted for undecylenic acid to serve as the "backbone" for the chiral monomer. Examples of naturally-occurring, readily available unsaturated fatty acids include palmitoleic acid, oleic acid, linoleic acid, linolenic acid, arachidonic acid, caproleic acid, elaidic acid, brassidic acid, erucic acid, nervonic acid, and vaccenic acid. The chemistry of attaching the chiral group to these unsaturated fatty acids, and their polymerization into chiral micelle polymers, will be essentially similar to that described above. Although preferred, the "backbone" of the monomer need not be a fatty acid or fatty acid derivative. Other amphophilic molecules could also be used for the "backbone," using methods known in the art of organic synthesis for attaching chiral groups to the backbone, and for polymerizing the chiral surfactant monomers into micelle polymers.

Various amino acids (or other chiral amine nucleophiles) can be substituted for valine to synthesize other surfactant monomers analogous to L-SUV, surfactant monomers that can then be polymerized to form other micelle polymers. More than one amino acid or other amine can be used in the monomer. All amino acids may be used as the chiral group, including alanine, valine, leucine, isoleucine, proline, tryptophan, phenylalanine, methionine, glycine, serine, threonine, tyrosine, cysteine, glutamine, asparagine, lysine, arginine, histidine, aspartic acid, glutamic acid, and modified amino acids. More than one amino acid residue may be attached to a fatty acid chain monomer, for example by repeating the amino acid linkage step to attach amino acids to multiple sites on the fatty acid chain, or by using a small peptide made with a peptide synthesizer, in either case producing a monomer with multiple chiral centers.

Other chiral molecules could be used in lieu of, or in addition to, amino acids, such as other chiral amines, or chiral alcohols, to form anionic, cationic, or neutral surfactant monomers. Examples of other chiral groups that could be used to add chiral centers to the "backbone" of the surfactant monomer include, for example, epinephrine, ephedrine, norephedrine, naproxen, warfarin, and phenylthiohydantion amino acid. Where appropriate, the chemistry used to attach the chiral group to the backbone will be modified using methods known in the art of organic synthesis.

In addition to γ-cyclodextrin, where desired other chiral selectors known in the art may be used to enhance the chiral separations obtained with the chiral micelle polymers. For example, the smaller α- or β-cyclodextrins could be advantageously used where a smaller analyte is being separated. Other water-soluble cyclodextrin compounds that may be used for this function include cyclodextrin polymers, carboxylic acid derivatives of a cyclodextrin, and hydroxypropyl- and hydroxyethyl- derivatives of α-, β-, and γ-cyclodextrins. Non-cyclodextrin chiral selectors may also be used as enhancers, including chiral crown ethers and bile salts.

It is preferred that the "three point rule" be followed to achieve enantioselectivity for a particular analyte.

Chiral micelle polymers in accordance with the present invention may also be used in liquid chromatography, for example as part of the mobile phase in a reversed-phase system employing a C-18 column. Especially in chromatographic systems, chiral micelle polymers in accordance with the present invention may be used on a preparative scale to purify large quantities of racemic mixtures. An additional advantage to using polymerized chiral micelles in liquid chromatography is that column back pressure should be reduced. In liquid chromatography with "conventional" micelles, chromatographic efficiency can be reduced due to high column back pressure attributable to coating of the stationary phase with surfactant monomers. Such coating should not occur with the polymerized micelles, because unpolymerized monomers are essentially absent.

Polymerized chiral micelles in accordance with the present invention could be used in otherwise-conventional liquid-liquid extraction systems, in which the polymerized chiral micelle is soluble only in one of the liquid phases. For example, poly (L-SUV) could be used in an aqueous phase extraction of a chiral compound that is soluble in an organic phase such as chloroform.

Polymerized chiral micelles in accordance with the present invention could also be used in a selective extraction medium or liquid membrane transport system, in which a polymerized chiral micelle preferentially transports one enantiomer across a membrane. For example, a membrane system could be constructed from a three-phase system comprising an aqueous phase containing a chiral micelle polymer and two organic phases, in which each of the three phases is immiscible in the other two, and in which the aqueous phase is intermediate in density between the two organic phases. The aqueous phase with the chiral micelle polymer acts as a transport membrane between the two organic phases. A racemic mixture dissolved in one of the organic phases could be resolved by selective transport through the aqueous membrane into the other organic phase.

Polymerized chiral micelles in accordance with the present invention could also be used in micelle-enhanced ultrafiltration. In this technique, micelles are added to an aqueous phase containing a racemic mixture. The aqueous mixture is then passed through an ultrafiltration membrane whose pore size is small enough to prevent micelles from passing through. The enantiomer with the higher affinity for the polymerized chiral micelle is enriched in the retainant, and the solution passing through the filter is enriched in the other enantiomer.

The present inventions will work not only with "normal" polymerized chiral micelles, but also with "reversed" polymerized chiral micelles. In a "normal" micelle in an aqueous or other polar solvent, the hydrophilic portions of the surfactant molecules are on the outside of the micelle, interacting with the polar solvent, while the hydrophobic portions of the surfactant molecules are on the inside of the micelle to form a nonpolar, pseudo-stationary phase. By contrast, in a "reversed" micelle in a nonpolar solvent, the hydrophobic portions of the surfactant molecules are on the outside of the micelle, interacting with the nonpolar solvent, while the hydrophilic portions of the surfactant molecules are on the inside of the micelle to form a polar, pseudo-stationary phase. The interior of a reversed micelle also typically contains a small amount of a polar solvent such as water. Conventional "reversed" micelles art well known in the art. "Reversed" polymerized chiral micelles will be useful in performing chiral separations. For example, poly (sodium N-undecylenyl-L-valinate) and poly (sodium N-undecylenyl-D-valinate) will also be used as "reversed" polymerized chiral micelles. When used as reversed micelles, the surfactant monomers will be synthesized in a minimum amount of water, and the polymerization will be performed in a nonpolar organic solvent such as cyclohexane. It should also be noted that the chiral center(s) need not be located in the hydrophilic portion of the surfactant, but may be in the hydrophobic portion of the molecules.

In chromatographic applications, polymerized chiral micelles in accordance with the present invention may be present in the mobile phase, or they could instead be incorporated into chiral stationary phases such as gels, wall coatings, and pack capillaries through means known in the art. For example, a gas chromatography capillary column may be packed with silica particles that have been coated with polymerized chiral micelles. Another possibility is the combination of a chiral mobile phase incorporating polymerized chiral micelles in accordance with the present invention, with a different chiral stationary phase. This combination can result in separation efficiencies that are greater than the sum of the parts.

Where a particular set of conditions results in the separation of two enantiomers, then the same or similar conditions should, in general, also successfully separate homologues of those enantiomers, as well as other enantiomers with similar structures.

Miscellaneous

The complete disclosures of all references cited in this specification are hereby incorporated by reference, as are the complete disclosures of each of the following two papers (neither of which is prior art to the present application): J. Wang and I. Warner, "Chiral Separations Using Micellar Electrokinetic Capillary Chromatography and a Polymerized Chiral Micelle," Anal. Chem., vol. 66, pp. 3773–3776 (Nov. 1, 1994); and J. Wang and I. Warner, "Combined Polymerized Chiral Micelle and γ-Cyclodextrin for Chiral Separation in Capillary Electrophoresis," J. Chromatogr., in press.

We claim:

1. A process for separating a mixture of two enantiomers; said process comprising transporting the enantiomers through a medium comprising polymerized chiral micelles and a chiral selector, or transporting the enantiomers and a medium comprising polymerized chiral micelles and a chiral selector over a substrate; wherein said micelles have differing affinities for the two enantiomers; wherein said chiral selector has differing affinities for the two enantiomers, and said chiral selector is not a polymerized chiral micelle; and wherein the differing affinities cause the two enantiomers to move through the medium or over the substrate at different velocities; whereby the enantiomers become separated from one another.

2. A process as recited in claim 1, wherein said transporting step comprises performing liquid chromatography.

3. A process as recited in claim 1, wherein said transporting step comprises performing capillary electrophoresis.

4. A process as recited in claim 1, wherein said transporting step comprises performing a liquid-liquid extraction between two immiscible liquid phases, wherein said micelles are substantially soluble in only one of the two liquid phases.

5. A process as recited in claim 1, wherein said transporting step comprises performing gas chromatography.

6. A process as recited in claim 1, wherein said transporting step comprises transporting the enantiomers and said micelles across a membrane.

7. A process as recited in claim 1, wherein said chiral selector comprises a chiral cyclodextrin.

8. A process as recited in claim 1, wherein said chiral selector comprises a crown ether.

9. A process as recited in claim 1, wherein said chiral selector comprises a bile salt.

10. A process as recited in claim 1, wherein said micelles comprise a polymer of monomers wherein each of said monomers comprises an unsaturated hydrocarbon chain linked to a chiral amino acid.

11. A process as recited in claim 1, wherein said micelles comprise a mixture of different polymerized chiral micelles.

12. A process as recited in claim 1, wherein said micelles comprise a co-polymer of different chiral surfactant monomers.

13. A process as recited in claim 1, wherein said micelles comprise reversed polymerized chiral micelles.

14. A process as recited in claim 1, wherein said micelles comprise poly (sodium N-undecylenyl-L-valinate), or comprise poly (sodium N-undecylenyl-D-valinate).

* * * * *